United States Patent [19]

Shimaoka

[11] Patent Number: 5,400,139
[45] Date of Patent: Mar. 21, 1995

[54] METHOD AND APPARATUS FOR ESTIMATING A MIXING PROPORTION OF DIFFERENT POWDERY CONTENTS

[75] Inventor: Haruo Shimaoka, Nara, Japan

[73] Assignee: Shimadzu Corporation, Kyoto, Japan

[21] Appl. No.: 125,166

[22] Filed: Sep. 23, 1993

[30] Foreign Application Priority Data

Sep. 28, 1992 [JP] Japan .................. 4-257878

[51] Int. Cl.⁶ .............................................. G01N 15/02
[52] U.S. Cl. .................................. 356/336; 356/343
[58] Field of Search .................. 356/343, 39, 335–342; 250/564, 574, 222.2; 364/555; 377/555; 73/865.5, 865.8, 866

[56]  References Cited

U.S. PATENT DOCUMENTS

| 3,315,066 | 4/1967 | Muta et al. ........................ 356/335 |
| 4,078,863 | 3/1978 | Eriksson et al. ................... 356/336 |
| 4,274,741 | 6/1981 | Cornillault ......................... 356/336 |
| 4,313,929 | 2/1982 | Morita et al. ...................... 356/340 |
| 4,779,003 | 10/1988 | Tatsuno ............................. 356/336 |
| 5,185,641 | 2/1993 | Igushi et al. ....................... 356/336 |

FOREIGN PATENT DOCUMENTS

| 0115950 | 5/1991 | Japan .................................. 356/336 |
| 3251741 | 11/1991 | Japan .................................. 356/336 |
| 4084736 | 3/1992 | Japan .................................. 356/336 |
| 4191640 | 7/1992 | Japan .................................. 356/336 |

Primary Examiner—Hoa Q. Pham
Attorney, Agent, or Firm—Nikaido, Marmelstein, Murray & Oram

[57] ABSTRACT

A method and apparatus which measures a particle size distribution of each content of powdery contents. Particle size distributions of a plurality of mixtures are calculated by blending the contents in various proportions, referring to the previously measured particle size distribution of each content, then determining the relationship between particular particle sizes in the plurality of particle size distributions and a mixing proportion. A particle size distribution of a mixture blended with the contents is measured, finding the particular particle size in the previously calculated particle size distributions of the mixture, and an actual mixing proportion of the contents in the mixture is estimated from the found particle size and the relations previously determined.

6 Claims, 2 Drawing Sheets

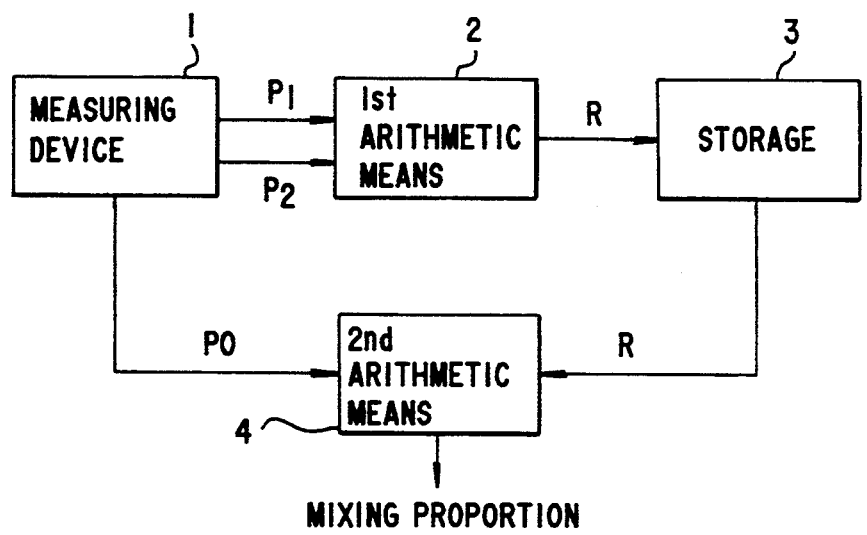
Fig.1
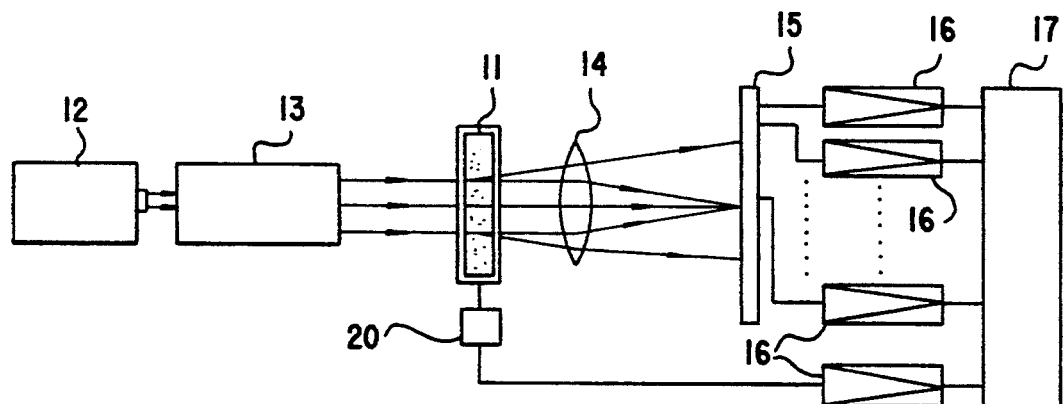
Fig.2
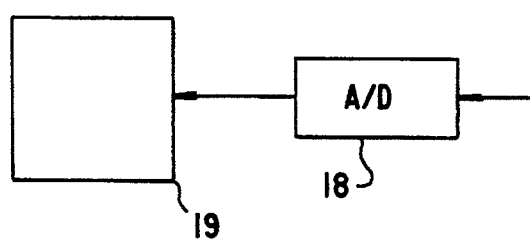

METHOD AND APPARATUS FOR ESTIMATING A MIXING PROPORTION OF DIFFERENT POWDERY CONTENTS

FIELD OF THE INVENTION

BACKGROUND OF THE INVENTION

The present invention relates generally to a system for estimating a mixing proportion of two kinds of powdery solids (hereinafter called "powdery contents" or "contents") present in the mixture thereof. More particularly, the present invention relates to a method and apparatus for estimating a mixing proportion of two kinds of powdery contents present in the mixture so as to ascertain if the mixture contains contents in a predetermined proportion.

By referring to FIG. 5, the background will be described:

FIG. 5 shows an undersize distribution (%) in which two kinds of powdery solids (a) and (b) having particle size distributions of large difference. The size distributions are depicted in dotted lines distant from each other with a flat portion (F) on the relative particle weight curve (c). This instance is advantageous in that the flat portion (F) can be used to estimate a mixing proportion of contents from a relative particle weight (%) corresponding to the flat portion (F).

A disadvantage is that this method cannot be applied to a case where the two different contents have particle size distributions which overlap each other as shown in FIG. 6. At present there is no effective method available to estimate a mixing proportion in such cases.

SUMMARY OF THE INVENTION

The present invention is directed to overcome the difficulty in estimating a proportion of powdery contents whose particle size distributions overlap each other, and is to provide a system for estimating a mixing proportion of contents in the mixture thereof.

According to the present invention, the method includes the steps of measuring a particle size distribution of each content, calculating particle size distributions of a plurality of mixtures obtained by blending the contents in various proportions, by referring to the previously measured particle size distribution of each content, determining the relations between a particular particle sizes in the plurality of particle size distributions and a mixing proportion, measuring a particle size distribution of a mixture blended with the contents, finding the particular particle size in the previously calculated particle size distributions of the mixture, and estimating an actual mixing proportion of the contents in the mixture from the found particle size and the relations previously determined.

According to another aspect of the present invention, the particle size distribution measuring apparatus includes a first means for measuring a particle size distribution of each content, a first arithmetic means for storing the measured particle size distribution of each content, calculating particle size distributions of a plurality of mixtures obtained by blending the contents in various proportions, and determining the relations between a particular particle sizes in the plurality of particle size distributions and a mixing proportion, a storage for storing the relations between a particular particle sizes in the plurality of particle size distributions and a mixing proportion; and a second arithmetic means for storing a particle size distribution of a mixture blended with the contents which is measured by the first measuring means, and determining a mixing proportion of the mixture on the basis of the particular particle sizes and the relations stored in the storage.

BRIEF DESCRIPTION OF THE DRAWINGS

This invention may be better understood and its numerous objects and advantages will become apparent to those skilled in the art by reference to the accompanying drawings as follows:

FIG. 1 is a diagrammatic view exemplifying the basic principle of the present invention;

FIG. 2 is a diagrammatic view showing an example of the apparatus according to the present invention;

DETAILED DESCRIPTION OF THE PREFERRED EMBODIMENT

Figure 3:
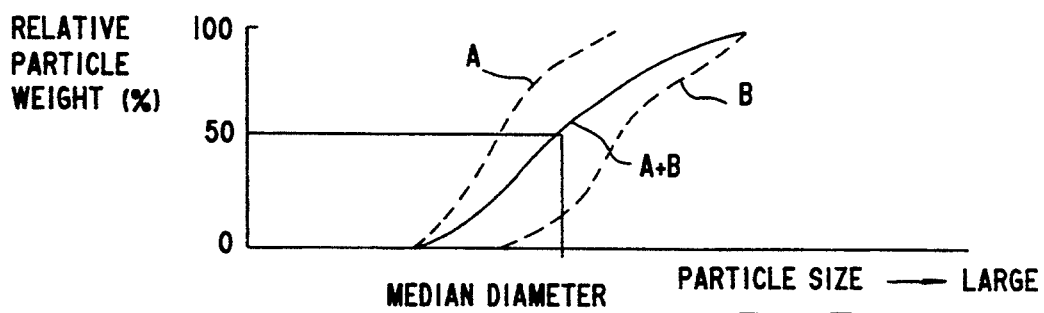
FIG. 3 is a graph showing a difference in the particle size distributions of samples (A) and (B) between before blending and after blending.

Referring to FIG. 1, the exemplary measuring device 1 includes a first arithmetic means 2, a storage 3, and a second arithmetic means 4. The measuring device 1 measures a particle size distribution of each content. The measured values $P_1$ and $P_2$ are input to the first arithmetic means 2. Several mixtures are made by blending the samples in various proportions, and the particle size distributions of these mixtures are calculated. The first arithmetic means 2 determines relations a particular particle size in the calculated particle size distributions and a mixing proportion. The storage 3 stores the relations determined in this way. The measuring device 1 measures a particle size distribution of each mixture containing contents in an unknown proportion. The measured values $P_0$ are input to the second arithmetic means 4 which seeks the particular particle size in the measured values $P_0$ and calculates a mixing proportion of the mixture by reference to the relations stored in the storage 3.

Referring to FIG. 2, the measuring device 1 is based on the diffraction/scattering theory. Powdery contents in homogeneous dispersion in a medium are caused to flow through a flow cell 11 in a direction perpendicular to the paper. The powdery solids in the flow cell 11 are irradiated with laser light in parallel generated by a laser 12, and are forced to have a predetermined cross-sectional area through a beam forming system 13.

A condenser lens 14 is disposed on the opposite side to the laser 12 with the flow cell 11 being interposed therebetween and a ring detector 15 is disposed on the focal surface of the condenser lens 14. An image of the powdery contents is formed on a light receptive surfaces of the ring detector 15 by diffraction or diffraction and scattering.

The ring detector 15 includes a plurality of photosensors each having ring-shaped light receptive surfaces on a substrate, the photo-sensors being arranged concentric with the optical axis of the laser light. A spatial intensity distribution is obtained from the varying outputs of the photo-sensors. The outputs of the photo-sensors are amplified by respective amplifiers 16, and are digitized by an A/D converter for storing in a computer 19.

Another photo-sensor 20 is provided adjacent to the flow cell 11 so as to measure light scattering sideways at relatively large angles from the powders therein. The output of the photo-sensor 20 is also amplified by the amplifier 16, and digitized by the A/D converter 18 through a multiplexor 17. Finally the computer 19 stores the digitized data in its storage.

The computer 19 obtains data on a spatial intensity distribution of laser light with which the contents are irradiated, the laser light being subjected to diffraction and scattering due to the presence of powdery solids. The computer 19 includes a first program whereby the data obtained are converted into a particle size distribution of the powders by a known arithmetic method on the basis of the Fraunhofer's diffraction theory or the Mie light scattering theory.

In addition to the first program, the computer 19 contains a second program whereby a mixing proportion is arithmetically estimated:

The second program contains (1) a preparatory routine which determines relations between a proportion of contents in a mixture and a particular reference such as a median diameter, and (2) an estimation routine which calculates a mixing proportion in a mixture. An operator selects one after another.

In operation, the operator prepares two kinds of powdery solids to be blended, hereinafter referred to as "sample (A)" and "sample (B)", and selects the preparatory routine in which samples (A) and (B) are separately introduced into the flow cell 11 so as to measure the particle size distribution independently. The computer 19 stores each data in the storage.

Figure 4:
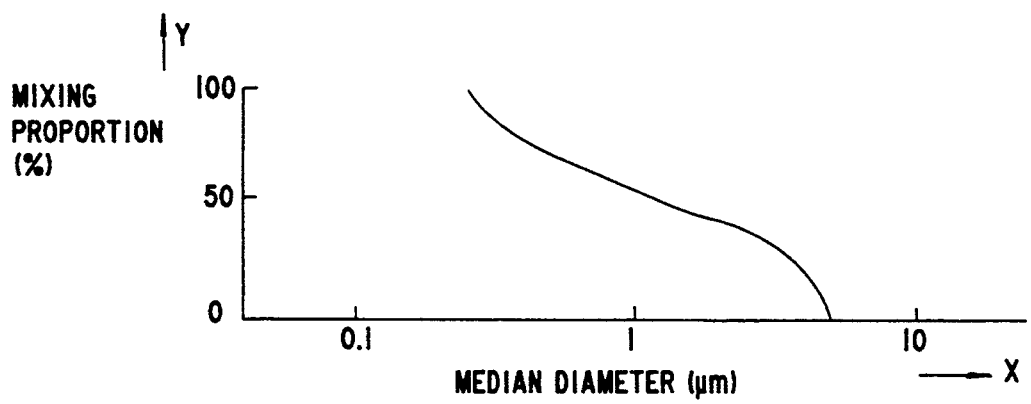
FIG. 4 is a graph showing the relations between mixing proportions obtained from the particle size distributions of samples (A) and (B) and the median diameters thereof.
Figure 5:
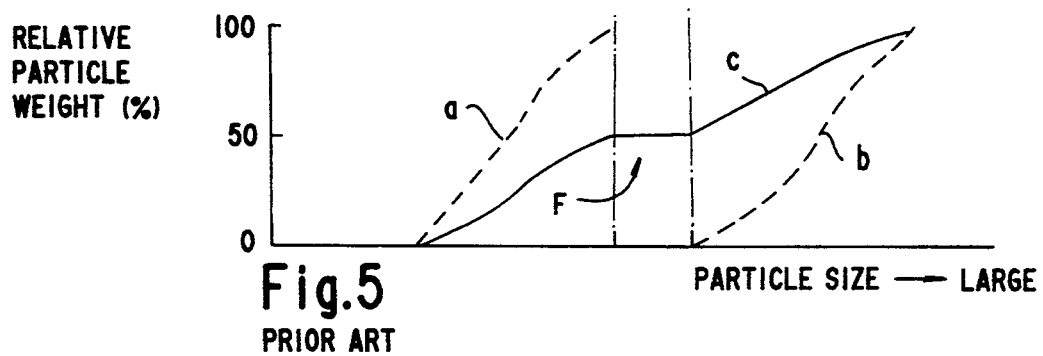
FIG. 5 is a graph showing an example of particle size distribution after the powdery contents having no overlapping distributions are blended.
Figure 6:
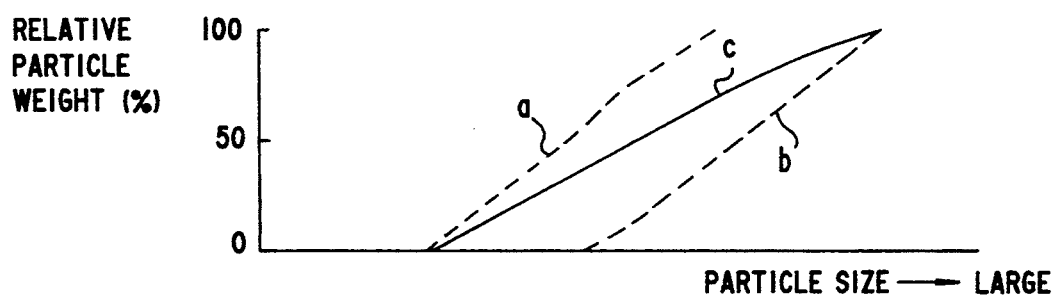
FIG. 6 is a graph showing an example of particle size distribution after the powders having overlapping distributions are blended.

Then the computer 19 calculates a particle size distribution of a mixture of sample (A) and (B) on the basis of the stored data on the particle size distributions of the samples. When the particle size distribution of each sample is generally known in the art, it is easy to calculate a particle size distribution of the mixture by weighted addition, that is, by totalling the particle size distributions of the samples with the addition of a weight in terms of the proportion of each sample in the mixture. As is evident from FIG. 3, when samples (A) and (B) are blended in the proportion of 1 to 1, which means that the proportion of sample (A) is 50%. Hereinafter, this percentage will be referred to as "mixing proportion". In FIG. 3, the particle size distribution of the mixture is indicated by the full line. Then the computer 19 determines median diameters (x) from the particle size distribution of the mixture, and also determines relations between the median diameters (x) and the mixing proportions (y). The relations are depicted in graph in FIG. 4, and the computer 19 stores this relations in terms of the following equation:

$$y = ax^3 + bx^2 + cx + d \qquad (1)$$

Variables a, b, c, and d are variables associated with a particular cubic curve.

In this way the preparatory routine is finished.

Then the estimation routine is selected. Samples (A) and (B) are blended, and the mixture is introduced into the flow cell 11. At this stage the proportion of samples (A) and (B) in the mixture is unknown. The estimation routine measures a spatial intensity distribution of laser light with which the contents in the flow cell 11 are irradiated.. The laser light is subjected to diffraction/scattering due to the presence of the powdery solids, and after the measured spatial intensity distribution is converted into a particle size distribution, a median diameter (x) of the particle size distribution is taken and put in the equation (1) stored in the computer 19. Thus the proportion (y) of samples (A) and (B) is obtained.

The estimated proportion (y) of samples (A) and (B) exhibits a reliable FIGURE as long as the measurement of the size distribution of the mixture are correct, and the mixing proportion can be estimated whether the size distributions of samples (A) and (B) may overlap or not.

The present invention is not limited to the exemplary embodiment but for example the median diameter used in each routine may be replaced by an average diameter or by a particular particle diameter. Preferably, the median diameter or the average diameter is used as a parameter, because these are free from an error in measuring the size distribution.

In storing the relations between the particle diameters (x) (preferably, a median diameter or an average diameter) and the mixing proportions (y), it is not always necessary to use the equation (1) but it can be stored as a table to which a suitable value such as median diameter in the size distribution of a mixture is applied.

The apparatus according to the present invention does not necessarily require that it incorporates a computer. Instead, manual input is possible by use of a keyboard through which the size distribution data are input to a separate computer, and the same arithmetic operation is performed as in the example described above, so as to obtain data on the relations between the mixing proportions and the median diameters. It is also possible to calculate a median diameter on paper by reference to the size distribution of the mixture previously measured, and to estimate a mixing proportion on the basis of these data including the relations obtained by arithmetic operation.

What is claimed is:

1. A method for estimating a mixing proportion of two kinds of powdery contents blended in a mixture, the method comprising the steps of:
   measuring a particle size distribution of each content;
   calculating particle size distributions of a plurality of mixtures obtained by blending the contents in various proportions, by referring to the previously measured particle size distribution of each content;
   determining the relations between a particular particle size in the plurality of particle size distributions and a mixing proportion;
   measuring a particle size distribution of a mixture blended with the contents;
   finding the particular particle size in the previously calculated particle size distributions of the mixture; and
   estimating an actual mixing proportion of the contents in the mixture from the found particle size and the relations previously determined.

2. The method according to claim 1, wherein the particular particle size is a median diameter.

3. The method according to claim 1, wherein the particular particle size is an average diameter.

4. The method according to claim 1, wherein the relations between a particular particle size in the plurality of particle size distributions and a mixing proportion is expressed by:

$$y = ax^3 + bx^2 + cx + d$$

where y is an estimated mixing proportion and x is the particular particle size, and where a, b, c, and d are variables associated with a particular cubic curve.

5. An apparatus for estimating a mixing proportion of two kinds of powdery contents blended in a mixture, the apparatus comprising:

a first means for measuring a particle size distribution of each content;

a first arithmetic means for storing the measured particle size distribution of each content, calculating particle size distributions of a plurality of mixtures obtained by blending the contents in various proportions, and determining the relations between a particular particle size in the plurality of particle size distributions and a mixing proportion;

a storage for storing the relations between a particular particle size in the plurality of particle size distributions and a mixing proportion; and a second arithmetic means for storing a particle size distribution of a mixture blended with the contents which is measured by the first measuring means, and determining a mixing proportion of the mixture on the basis of the particular particle size and the relations stored in the storage.

6. The apparatus according to claim 5, wherein the first means comprises an optical system for irradiating the contents afloat in dispersion with laser light, and measuring a spatial intensity distributions of the laser light which diffracts and scatters owing to the powdery contents, and an arithmetic means for converting the spatial intensity distribution into a particle size distribution of the contents.

* * * * *